United States Patent
Gustafsson

(10) Patent No.: US 6,448,465 B1
(45) Date of Patent: Sep. 10, 2002

(54) SANITARY NAPKIN WITH A LONGITUDINALLY CURVING STIFFENING ELEMENT

(75) Inventor: Anders Gustafsson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/445,182

(22) PCT Filed: May 13, 1998

(86) PCT No.: PCT/SE98/00883

§ 371 (c)(1),
(2), (4) Date: Dec. 8, 1999

(87) PCT Pub. No.: WO99/00081

PCT Pub. Date: Jan. 7, 1999

(30) Foreign Application Priority Data

Jun. 26, 1997 (SE) ................................................ 9702463

(51) Int. Cl.⁷ .......................... A61F 13/15; A61F 13/20
(52) U.S. Cl. ................... 604/367; 604/378; 604/385.01
(58) Field of Search ................................ 604/358, 367, 604/378, 385.01, 385.17

(56) References Cited

U.S. PATENT DOCUMENTS

| 4,195,634 A | * | 4/1980 | DiSalvo et al. ............. 128/290 |
| 4,790,838 A | | 12/1988 | Pigneul et al. ............. 604/366 |
| 4,804,380 A | | 2/1989 | Lassen et al. ............. 604/385.1 |
| 4,865,597 A | | 9/1989 | Mason, Jr. et al. ......... 604/385.1 |
| 5,197,959 A | | 3/1993 | Buell ........................ 604/385.1 |
| 5,300,055 A | * | 4/1994 | Buell ........................ 604/385.1 |
| 5,591,150 A | | 1/1997 | Olsen et al. ............... 604/385.1 |
| 6,198,091 B1 | * | 3/2001 | Hansson et al. ............ 604/378 |

FOREIGN PATENT DOCUMENTS

WO  94/10956  5/1994

* cited by examiner

Primary Examiner—John G. Weiss
Assistant Examiner—Michele Kidwell
(74) Attorney, Agent, or Firm—Burns, Doane, Swecker & Mathis, L.L.P.

(57) ABSTRACT

An absorbent article with an absorbent body enclosed between inner and outer casing sheets and a stiffening element extending from the rear, through the intermediate, and into the front part of the article. The stiffening element's front and rear parts are broader than its intermediate part and the stiffening element is not wider than 4 cm at its front to intermediate transition region. Side flaps are formed by at least some parts of the remainder of the article which extend laterally beyond the stiffening element, so that the distance between side-edges of the stiffening element and an edge of the side flap varies within the region. The stretch resistance of the side flaps is greater than the stiffening element's longitudinal bending resistance, so inward pressing of the side flaps causes the stiffening element to curve longitudinally, to obtain an upwardly concave shape adapted to the shape of a wearer's body.

14 Claims, 2 Drawing Sheets

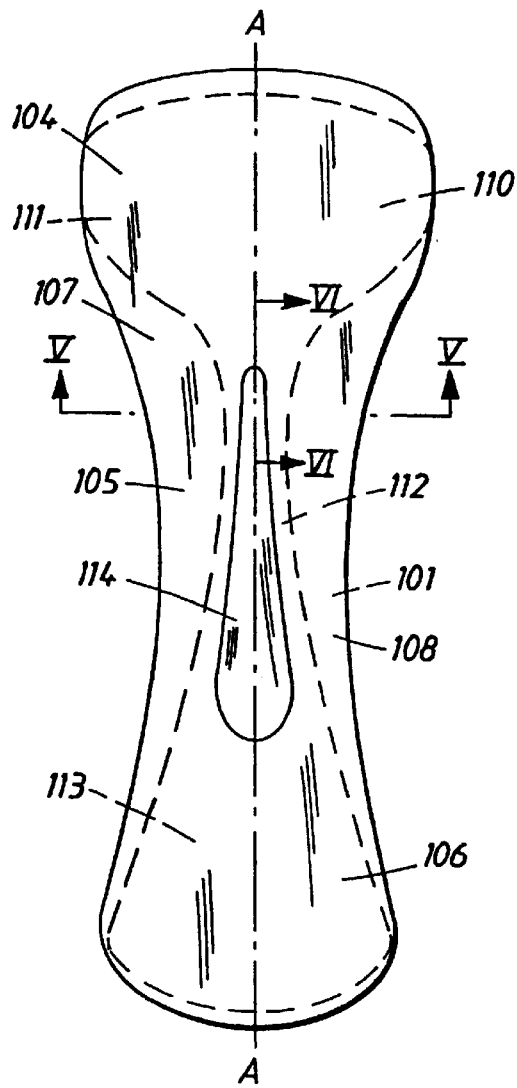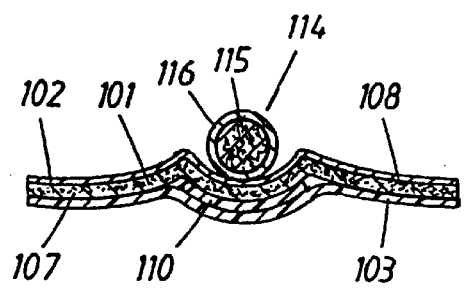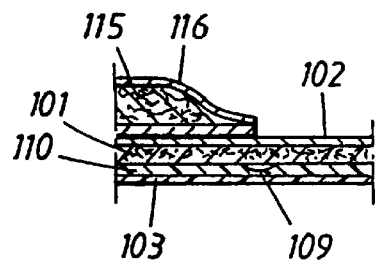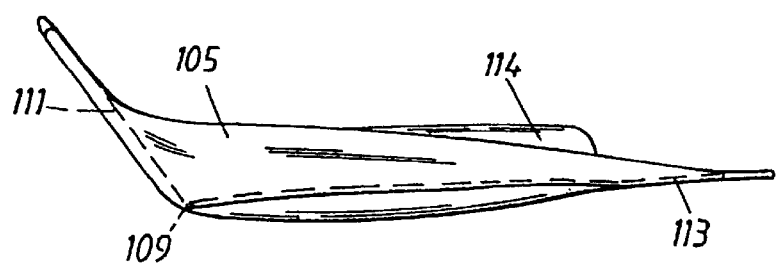

SANITARY NAPKIN WITH A LONGITUDINALLY CURVING STIFFENING ELEMENT

The present invention relates to an absorbent article in the form of a sanitary napkin or in the form of a female incontinence guard for light incontinence, comprising an absorbent body which is enclosed between an inner and an outer casing sheet, which article has a front part, a rear part and an intermediate part.

Sanitary napkins and like products shall have in use a three-dimensional shape that is adapted to the shape of the wearer's body. However, such articles are normally produced and packaged in a flat state. It is known to provide sanitary napkins and like articles with elastic devices that give the napkins a three-dimensional shape when the napkins are removed from their respective packets. The application of elastic devices complicates the process of manufacture and may cause the napkin to be deformed permanently in its packet, and are also liable to cause chafing of the wearer's skin. There is thus a need for sanitary napkins that include means other than elastic devices for imparting a three-dimensional shape to the napkin.

The absorbent body of a sanitary napkin or like article is also very liable to be deformed in an uncontrolled manner as the wearer moves. Because the absorbent body is compressed by the wearer's thighs, the absorbent body is liable to be pleated or broken and/or pleats or folds are liable to form in the inner casing sheet. Such weakenings and pleats considerably increase the risk of leakage.

Another problem associated with the deformation and compression of the absorbent body is that the sanitary napkin can be felt to be lumpy and uncomfortable in wear, and the edges of the sanitary napkin or sharp folds formed by said deformation are liable to chafe the wearer's skin.

In U.S. Pat. No. 4,865,597, an absorbent product having a reinforcing member is disclosed. The reinforcing member is resiliently compressible and returns the absorbent product to its original shape after lateral compression of the product during use.

U.S. Pat. No. 5,591,150 and U.S. Pat. No. 5,197,959 disclose absorbent articles having components which respond to laterally compressive forces by compressing in a transverse direction in order to form a longitudinally extending bulge or ridge on the body-contacting surface of the articles.

U.S. Pat. No. 4,790,838 teaches a sanitary napkin of the aforedescribed kind which is brought to a three-dimensional shape in use without the aid of elastic devices. According to this prior publication, those parts of the casing sheets that lie outside the edges of the absorbent body provide effective lateral tightness of the napkin, at the same time as said parts in combination with two biconcave compression lines in the centre part of the absorbent body deform said body laterally in use, so as to form a central basin-shaped part. There is a serious risk with a napkin of this kind that gaps will be formed between the absorbent body and the wearer's skin in the region within which liquid is discharged. Such gaps impair the ability of the napkin to carry away liquid quickly from the acquisition surface, which can result in the napkin feeling moist and uncomfortable to the touch. Furthermore, control of discharged liquid is made difficult, because there is a serious risk that instead of being absorbed directly by the absorbent body, liquid will run on the top surface of the napkin in a direction towards the lowest point thereof, this point being dependent on the attitude of the wearer's body. The risk of the absorbent body pleating and weakening due to deformation resulting from movement of the wearer is relatively significant in the case of such a napkin.

The object of the present invention is to eliminate the aforesaid problems.

This object is achieved in accordance with the invention with an absorbent article in accordance with claim 1.

In a first embodiment, the distance between the edge of those parts of the remainder of the napkin that lie laterally outside the stiffening element and adjacent side-edges of the stiffening element is at least 2 cm at the narrowest section of the stiffening element, and the absorbent body has the same extension as the stiffening element, wherein those parts of the napkin that lie laterally outside respective side-edges of the stiffening element are comprised solely of mutually joined casing sheets. In a first variant, the stiffening element is comprised of absorbent material. In a second variant, the stiffening element is comprised of a non-absorbent material and is placed closest to the outer casing sheet which faces outwards in use, i.e. faces away from the wearer's body. The stiffening material is preferably comprised of a liquid-impervious material. The edges of those parts of the article that lie laterally outside the stiffening element are preferably straight in the intermediate part of the stiffening element.

In a second embodiment, the absorbent body includes a sheet of highly flexible absorbent material that extends around and beyond the periphery of the stiffening element, and the stiffening element has in its intermediate part and in portions of its rear part longitudinal edges that curve upwards in a direction from the outer casing sheet to the inner casing sheet. The stiffening element also has a thinner section at the transition between the front and the intermediate parts thereof and the absorbent body includes a central upstanding part which extends from the position of the transition between the front and intermediate parts of the stiffening elements somewhat into the rear part of the napkin. The edges of those parts of the napkin that lie laterally outside the stiffening element are preferably curved in the intermediate part of said element, in a direction towards respective side-edges thereof, and the edges of those parts of the napkin that lie laterally outside the stiffening element are located at the furthest distance from respective side-edges of the stiffening element at the narrowest section thereof.

The invention will now be described with reference to the accompanying drawings, in which FIG. 1 illustrates a first embodiment of an inventive sanitary napkin from above;

FIG. 4 is a schematic view of a second embodiment of an inventive sanitary napkin from above;

FIGS. 5 and 6 are sectional views taken on respective lines V—V and VI—VI in FIG. 4; and FIG. 7 is a side view of the napkin illustrated in FIG. 4, with side-edges of the napkin pressed inwards.

Figure 1:
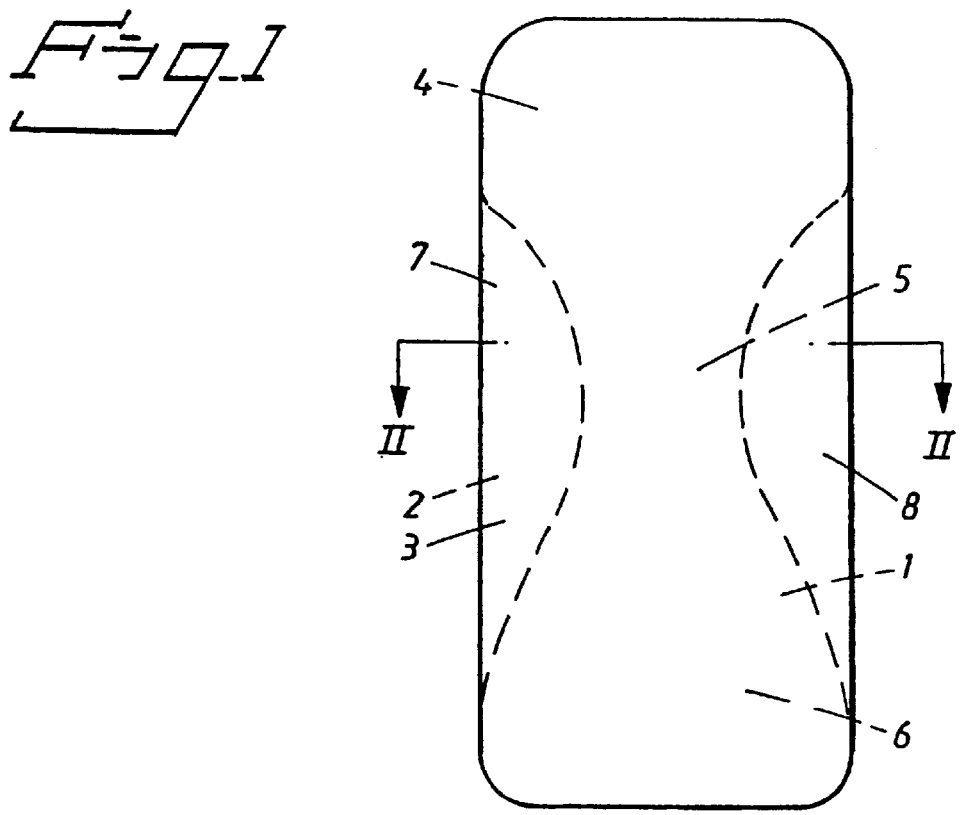
Figure 2:
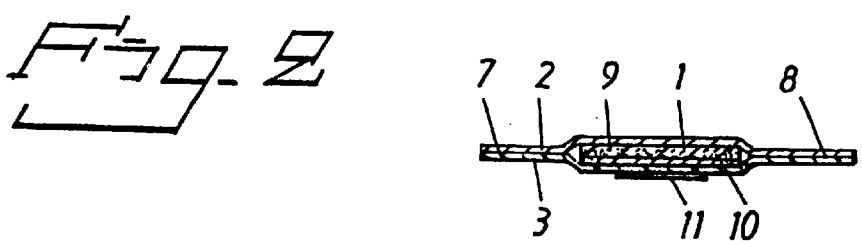
FIG. 2 is a cross-sectional view taken on the line II—II in FIG. 1.
Figure 3:
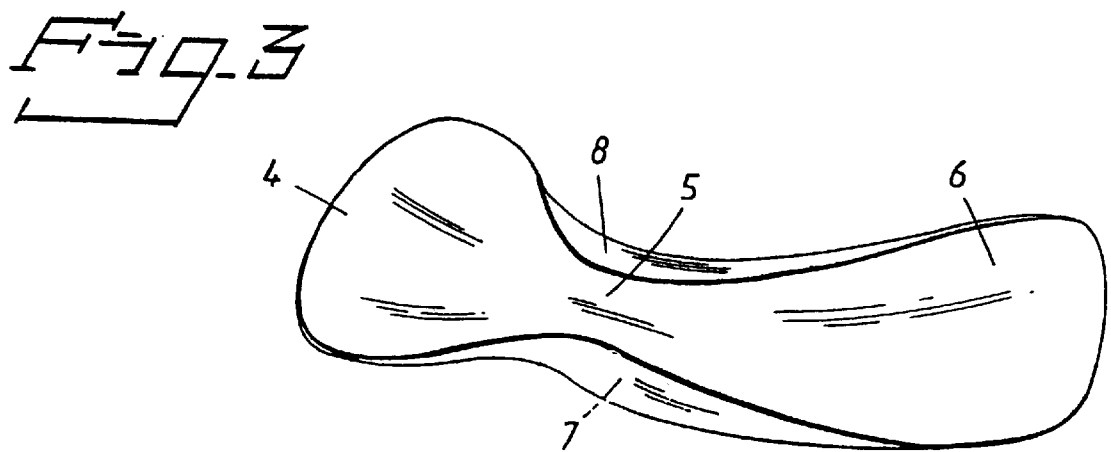
FIG. 3 is a perspective view of the napkin illustrated in FIGS. 1 and 2 from above and shows parts of the casing sheet pressed inwards.

The sanitary napkin illustrated in FIGS. 1–3 includes an absorbent body 1 enclosed between two casing sheets 2, 3. Seen from above, the absorbent body 1 has a keyhole-like shape that includes a front part 4, an intermediate part 5 and a rear part 6. The intermediate part 5 is narrower than the front and the rear parts 4 and 6 respectively, and has its narrowest part in the transition to the front part 4. The widest parts of the front and the rear parts of the illustrated napkin have mutually the same width. The casing sheets 2, 3 are essentially rectangular in shape with rounded edges and a width which is slightly larger than the largest width of the absorbent body. Those parts of the casing sheets that lie outside the side-edges of the absorbent body 1 are joined together, for instance glued. The casing sheets are fastened to the absorbent body at those sheet portions that overlap said body. As a result of this design, there are formed casing-sheet flaps 7, 8 that extend on both sides of the absorbent body 1 between the broadest points of its front and rear parts.

The absorbent body 1 includes a sheet or layer 9 of absorbent material, e.g. cellulose fluff either with or without an admixture of superabsorbent particles or other absorbent material of the kind normally used in absorbent articles, and also includes a stiffening element 10. The absorbent sheet 9 may be comprised of several layers. The stiffening element may be comprised of an absorbent or non-absorbent material. In the illustrated embodiment the stiffening element 10 has the same extensions as the absorbent body 1 and is comprised of a sheet of polyethylene plastic, which has a material rigidity of at least 400 MPa according to DIN 53457.

The illustrated sanitary napkin carries on its undersurface a typical adhesive coating 11 which enables the napkin to be secured to the inside of a pair of panties or knickers. The adhesive coating 11 is protected by a release foil or some like device prior to use, and extends only in the intermediate part 5 of the napkin. The casing sheet 2 lies proximal to the wearer's body in use and must therefore be permeable to liquid, so as to enable discharged liquid to be sucked into the absorbent body 1. This casing sheet shall have a soft surface. A suitable material for the casing sheet 2 is a soft, skin-friendly and highly flexible material of the type typically used as surface material on absorbent articles. Examples of such materials are perforated plastic film, woven textile material, nonwoven textile material, i.e. nonwoven material, textile or plastic nets produced by knitting, crocheting, braiding, moulding or corresponding processes. The outer casing sheet 3 will preferably also have a soft surface and may conveniently consist of the same material as the casing sheet 2. The flaps 7, 8 formed by the casing sheets shall have a relatively high stretch resistance while being highly flexible nevertheless. At least one of the casing sheets should therefore be made of a relatively rigid material. It may also be suitable to ensure that the casing sheet 3 is liquid-impervious, at least in those parts that project out from the absorbent body, either by suitable selection of material and/or by rendering at least said parts hydrophobic.

The narrowest portion of the intermediate part 5 of the absorbent body shall have a width in the range of 1–4 cm, preferably a width of about 3 cm. Measurements taken on sanitary napkin users have shown that there is a space-limiting, critical region in the groin region between two groups of muscles that run from the inside of the pelvic floor down along each thigh. It has surprisingly been found that the distance between these muscle groups in the genital region varies only to a small extent from person to person having mutually different body shapes and mutually different degrees of "plumpness". Even though the distance between a wearer's thighs is, of course, affected by fat, the distance between the muscle groups in the wearer's crotch will be essentially the same irrespective of whether the wearer is thin, of normal weight, or overweight. The distance between these muscle groups has been found to vary between 3 and 3.5 cm.

Tests have shown that the unpleasantness experienced by a wearer in the form of pressure or chafing against the insides of the thighs is dependent on whether or not the width of the napkin in said critical region markedly exceeds the distance between the aforesaid muscle groups. It has also been found in this respect that the majority of users will feel a sanitary napkin to be uncomfortable, when the width of the critical region exceeds 4 cm in use. This critical region extends from 0.5 cm to 1.5 cm in the longitudinal direction of the napkin.

A sanitary napkin is applied, or put on, by first fastening it in a pair of panties, or knickers, with the aid of the adhesive coating 11. The panties are then pulled up until the napkin comes into abutment with the wearer's body. The flaps 7, 8 will be pressed upwards and inwards, i.e. towards one another, by the wearer's thighs, during and after applying the napkin. The effect of this inward pressing of the flaps 7, 8 is illustrated schematically in FIG. 3. As will be evident from FIG. 3, this inward pressing of the flaps 7, 8 causes the absorbent body to curve longitudinally so as to obtain the illustrated upwardly concave shape adapted to the shape of the wearer's body. The forces exerted on the absorbent body act in the same direction as that in which the outer edges of the flaps extend. Thus, in the initial stage of the inward pressing of the flaps the absorbent body is subjected on both sides to the tension forces that act towards each other in the broadest points of the front and the rear part of the napkin, whereas the forces are directed obliquely inwards in the final stage of this inward pressing of the flaps. As mentioned in the aforegoing, the absorbent body must be relatively rigid, in order to prevent these forces from pleating or compressing the absorbent body.

However, the absorbent body need not be so rigid as to cause the resistance to longitudinal bending to be greater than the stretch resistance or the mechanical strength of the flap material. The rigidity of the absorbent body is determined by the material in the stiffening element.

It will be understood that the curvature of the absorbent body is contingent on the extent to which the edges of the flaps are pressed inwards when putting on the napkin. The napkin can be constructed to obtain the desired radius of curvature such as to obtain a three-dimensional shape adapted to the wearer's body, by varying the width of the front and the rear part of the absorbent body.

Because the width of the absorbent body and stiffening element will preferably be such as to ensure that their edges will not come into contact with the wearer's thighs, or legs when putting on the napkin, the risk of these edges chafing against the wearer's skin is very small. This makes the described sanitary napkin very comfortable to wear.

The stiffening element 10 of the illustrated embodiment is comprised of a liquid-impervious material. If the stiffening element is made from an absorbent material instead, e.g. a rigid absorbent foam or a dry-defibred fibre sheet of high density and stiffness of the type describe din WO 94/10953 and WO 94/10956, the liquid imperviousness outwards of the napkin must be ensured in some other way, for instance by forming the outwardly facing casing sheet 3 from liquid-impervious material, e.g. a plastic material or vapour-permeable nonwoven material. Alternatively, a liquid-impervious sheet or layer may be placed nearest the casing sheet 3.

In the preferred embodiment, the stiffening element 10 has the same shape and size as the absorbent sheet 9. This is not completely necessary, since it is sufficient for the sheet 10 to extend longitudinally from the widest portions of the front part of the absorbent body to the widest portions of the rear part of said body.

FIGS. 4–7 illustrate a second embodiment of an inventive sanitary napkin. The sanitary napkin shown in these Figures includes an absorbent sheet 101 enclosed between a liquid-pervious inner casing sheet 102 and a liquid-impervious outer casing sheet 103. The casing sheets and the absorbent sheet may be comprised of the same material as corresponding components in the embodiment described with reference to FIGS. 1–3, but with the limitation that the absorbent sheet 101 shall be highly flexible and therefore not too thick. When see from above, the sheet 101 has a keyhole-like shape that includes a front part 104, an intermediate part 105 and a rear part 106. A stiffening element 110 is disposed between the outer casing sheet 103 and the absorbent sheet 101. The stiffening sheet 110 also has a keyhole-like shape that includes a front part 111, a rear part 113 and an intermediate part 112. As will be evident from FIG. 4, the intermediate part of the stiffening sheet is much narrower than the intermediate part of the absorbent sheet 101. The width of the stiffening element in its narrowest section in the transition between the front and intermediate parts 11 and 112 respectively is less than 4 cm and preferably about 3 cm. Those portions of the casing sheets 102, 103 and of the absorbent sheet 101 that project out laterally beyond the stiffening element together form side-flaps 107, 108.

The stiffening element 110 is preferably comprised of plastic material, e.g. polyethylene plastic, and the intermediate part 112 of the stiffening element has an outwardly curved shape, as evident from FIG. 5. This upward curvature of the stiffening element extends from the intermediate part 112 into the rear part 113 and tapers-off successively at the end of the rear part of said element. The upward curvature of the stiffening element is adapted to conform to the wearer's anatomy. As a result of this design of the intermediate part of the stiffening element, any forces acting transversely on the napkin will be taken up by bending of the stiffening element and the absorbent sheet 101, without risk of pleating, weakening or compressing said sheet. The front part 111 is flat when the napkin is free from load.

As will be evident from FIG. 6, the stiffening element has a transverse section 109 of reduced material thickness, this element section constituting "hinge means", as described hereinafter.

The sanitary napkin illustrated in FIGS. 4–7 also includes a separate, elongated absorbent body 114 that extends from the transition region between the front part 104 and the intermediate part 105 of the sheet 101 slightly into the rear part 106, as apparent from FIG. 4. The absorbent body is disposed on top of the casing sheet 102 and its ends are fastened to said sheet in some suitable fashion. The absorbent body 114 of the illustrated embodiment is comprised of an absorbent core 115, for instance cellulose fluff contained in a liquid-permeable casing 116, for instance a nonwoven casing. The body 114 is positioned symmetrically in relation to a longitudinal symmetry line A–A and has a lateral extension that is smaller than the lateral extension of the intermediate part 112 of the stiffening element 110. When the sanitary napkin shown in FIGS. 4–7 is worn, the absorbent body 114 will lie against the wetting point of the wearer's body, i.e. that region of the napkin within which body liquid is delivered, thereby enhancing the leakage security of the napkin.

FIG. 7 is a side view of the napkin shown in FIGS. 4–6, with the flaps folded up, of which flap 105 is shown in the Figure. As a result of the hinge means 109, the front part 111 of the stiffening element will be folded upwards as the flaps 105, 106 are folded upwards, and form with the remainder of the stiffening element an angle that is contingent on the extent to which the flaps are folded upwards and on the distance of the flap edges from the side-edges of the stiffening element. This sanitary napkin will conform well to the wearer's anatomy when applied.

Because of the configuration and shape of the stiffening element 110 in use, and because the side-flaps 105, 106 extend in the fold between the wearer's thighs and lower body, the sanitary napkin illustrated in FIGS. 4–7 need not be fastened to the wearer's panties, or knickers, in order to be held in place when worn. This also applies to the sanitary napkin illustrated in FIGS. 1–3, therewith allowing the adhesive coating 11 to be omitted if desired.

The upwardly folded side-flaps 7, 8 and 107, 108 respectively of the sanitary napkin prevent the wearer's thighs coming into direct contact with the edges of the stiffening element, therewith enhancing wearer comfort. The upwardly folded side-flaps also prevent edge leakage.

It will be understood that the described embodiment can be modified within the scope of the invention, particularly with respect to the shape and size of the front and rear parts of the stiffening element. The stiffening elements need not be single-piece structures, but may comprise several mutually joined pieces, which need not be comprised of mutually the same material. The stiffening element may also include longitudinally and/or transversely extending stiffening bars or may include thicker or thinner regions. The outer contours of the side-flaps may be adapted to the desired degree of bending of the stiffening element. The side-flaps may also consist of separate elements that are attached, at least at their ends, to the side-edges of the front and rear napkin parts. Neither is it necessary for the side-flaps to extend from the broadest portions of the front and the rear napkin parts. The important thing in this latter respect is that the distance between the narrowest section of the stiffening element and the outer edge of adjacent side-flap edges is sufficiently large to obtain desired bending of the stiffening element. Neither need the casing sheets be fastened to the stiffening element and to the absorbent body over the whole of their respective surfaces, but may solely be fastened to the absorbent body along edge zones extending along the contours of the body. In principle, it suffices to fasten the casing sheets to the absorbent body at two points on its front and rear part. When the casing sheets in their entirety extend beyond the absorbent body, it may suffice to fasten solely one of these sheets, preferably the outer casing sheet, to the absorbent body. When the article is a multi-sheet article and the stiffening element is comprised of an absorbent material, the stiffening element need not be placed nearest the outer casing sheet, but may instead lie between other absorbent sheets. Neither need the broadest portions of the front and rear parts of the absorbent body have mutually the same width. The sanitary napkin according to the first described embodiment may, of course, include an upstanding, elongated and centrally positioned absorbent body. The central, elongated absorbent body need not be a separate component, but may consist of a raised part of the absorbent material enclosed between the casing sheets, for example. The invention is therefore solely restricted by the contents of the following Claims.

What is claimed is:

1. An absorbent article, comprising:
    an absorbent body enclosed between an inner casing sheet and an outer casing sheet, said absorbent body having a front part, a rear part, and an intermediate part;
    a stiffening element which extends from the rear part of the absorbent body, through the intermediate part of the absorbent body and into the front part of the absorbent body, wherein the stiffening element is enclosed between the casing sheets, the stiffening element having a front edge, a rear edge, and two side edges, and the stiffening element includes a front part, a rear part and an intermediate part, wherein the front and rear parts of the stiffening element are broader than the intermediate part of the stiffening element; and side flaps extending on both sides of the stiffening element laterally outside said side edges of the stiffening element and along and adjacent to the side-edges of the stiffening element at least within a region that begins in the front part of the stiffening element and terminates in the rear part of the stiffening element, wherein a distance between the side-edges of the stiffening element and each respective edge of the absorbent article located laterally outside respective side-edges of the stiffening element varies within said region, wherein said stiffening element has a width of less than 4 cm in a transition region between the front and the intermediate parts of the stiffening element and said side flaps have a stretch resistance greater than a resistance of said stiffening element to bending in a longitudinal direction of the stiffening element, whereby inward pressing of said side flaps causes said stiffening element to curve longitudinally, so as to obtain an upwardly concave shape adapted to a shape of a wearer's body.

2. An absorbent article according to claim 1, wherein the distance between each respective edge of the absorbent article that extends laterally outside the stiffening element and adjacent side-edges of said stiffening element is at least 2 cm at a narrowest section of the stiffening element.

3. An absorbent article according to claim 2, wherein the absorbent body has a shape corresponding to a shape of the stiffening element, such that the side flaps extending laterally outside the side-edges of the stiffening element are comprised solely of mutually joined casing sheets.

4. An absorbent article according to claim 1, wherein the stiffening element is comprised of absorbent material.

5. An absorbent article according to claim 3, wherein the stiffening element is comprised of non-absorbent material and is placed nearest the outer casing sheet, which faces outwardly from a wearer's body when the absorbent article is worn.

6. An absorbent article according to claim 5, wherein the stiffening element is comprised of liquid-impervious material.

7. An absorbent article according to claim 1, wherein the absorbent body includes a sheet of absorbent, highly flexible material which extends around a periphery of the stiffening element and beyond said stiffening element.

8. An absorbent article according claim 1, wherein the stiffening element has upwardly curved longitudinal edges that extend from the outer casing sheet to the inner casing sheet in the intermediate part of the stiffening element and in portions of the rear part of the stiffening element.

9. An article according to claim 1, wherein the stiffening element has a thinner section at the transition region between the front part and the intermediate part of said stiffening element.

10. An article according to claim 1, wherein the absorbent body includes a central upstanding part which extends from the transition region between the front part and the intermediate part of the stiffening element slightly into the rear part of said absorbent body.

11. An absorbent article according to claim 1, wherein the side flaps that extend laterally outside the stiffening element are straight in the intermediate part of said stiffening element.

12. An article according to claim 1, wherein the edges of the side flaps that extend laterally outside the stiffening element in the intermediate part of said stiffening element are curved in a direction towards respective side-edges of the stiffening element; and wherein the edges of the side flaps that extend laterally outside the stiffening element are located furthest from respective side-edges of the stiffening element at the narrowest section of said stiffening element.

13. An absorbent article as in claim 1, wherein the absorbent article is a sanitary napkin.

14. An absorbent article as in claim 1, wherein the absorbent article is an incontinence guard for light incontinence.

* * * * *